United States Patent
Burris et al.

(10) Patent No.: US 8,241,586 B2
(45) Date of Patent: Aug. 14, 2012

(54) OPERATORY WATER DISINFECTION SYSTEM

(75) Inventors: William A. Burris, Pittsford, NY (US); Philip M. Prinsen, Ontario, NY (US)

(73) Assignee: Alab, LLC, Rush, NY (US)

( * ) Notice: Subject to any disclaimer, the term of this patent is extended or adjusted under 35 U.S.C. 154(b) by 1625 days.

(21) Appl. No.: 10/074,992

(22) Filed: Feb. 13, 2002

(65) Prior Publication Data
US 2002/0134736 A1    Sep. 26, 2002

Related U.S. Application Data

(60) Provisional application No. 60/269,403, filed on Feb. 16, 2001.

(51) Int. Cl.
*A61L 2/00* (2006.01)
*C02F 1/78* (2006.01)

(52) U.S. Cl. .......... 422/292; 422/305; 422/905; 422/62; 422/186.07

(58) Field of Classification Search .................. 422/292, 422/293, 305, 306, 905, 186.07, 186.12, 422/62
See application file for complete search history.

(56) References Cited

U.S. PATENT DOCUMENTS

| | | | | |
|---|---|---|---|---|
| 4,019,986 A * | 4/1977 | Burris et al. | .................. | 210/139 |
| 4,555,335 A | 11/1985 | Burris | ............................ | 210/192 |
| 5,120,219 A | 6/1992 | DeFarcy | ........................ | 433/88 |
| 5,151,250 A | 9/1992 | Conrad | | |
| 5,158,454 A | 10/1992 | Viebahn et al. | ................. | 433/82 |
| 5,207,993 A | 5/1993 | Burris | ........................... | 422/256 |
| 5,213,773 A | 5/1993 | Burris | ........................... | 422/256 |
| 5,422,043 A | 6/1995 | Burris | ........................ | 261/122.1 |
| 5,443,801 A * | 8/1995 | Langford | ...................... | 422/294 |
| 5,520,893 A | 5/1996 | Kasting, Jr. et al. | .......... | 422/305 |
| 5,529,760 A | 6/1996 | Burris | ....................... | 422/186.07 |
| 5,681,370 A * | 10/1997 | McMahon | ....................... | 95/105 |
| 5,709,546 A | 1/1998 | Waggoner | ....................... | 433/82 |
| 5,776,351 A | 7/1998 | McGuinness et al. | | |
| 5,824,243 A * | 10/1998 | Contreras | .................... | 261/36.1 |
| 5,858,283 A | 1/1999 | Burris | ........................ | 261/122.1 |
| 5,935,431 A | 8/1999 | Korin | ............................ | 210/205 |

(Continued)

FOREIGN PATENT DOCUMENTS

EP    1188473    3/2002

(Continued)

OTHER PUBLICATIONS

Prosecution history of Canadian Patent Application 2437486 which corresponds to U.S. Appl. No. 10/074,992.
European Patent EP1188473 by Morita et al. enclosed as a translation of WO0064568 by Morita et al., cited in prosecution of Canadian application 2437486.

(Continued)

*Primary Examiner* — Sean E Conley

(57) ABSTRACT

This ozone appliance for the professional dental office and other medical applications introduces dissolved ozone into dental and surgical operatory water lines. This dissolved ozone can not only disinfect water and water lines; it can also reduce gum bleeding, gingivitis, bad breath, teeth stains and oral bacteria. Additionally, it can aid in wound disinfection in surgery and attack microbial contamination of water from dental and surgical operatory water lines and attached hand pieces and dispensing devices by automatically killing waterborne germs and destroying biofilms where germs can hide and grow. It can, therefore, be used to disinfect water lines in dental operations and for other medical applications such as providing liquid containing ozone for cleaning and disinfecting skin prior to surgery (and tissue exposed during surgery). Further, a unit connected to operatory water lines can give an audible or other alarm if the water becomes unsafe.

30 Claims, 15 Drawing Sheets

U.S. PATENT DOCUMENTS

Figure 4:
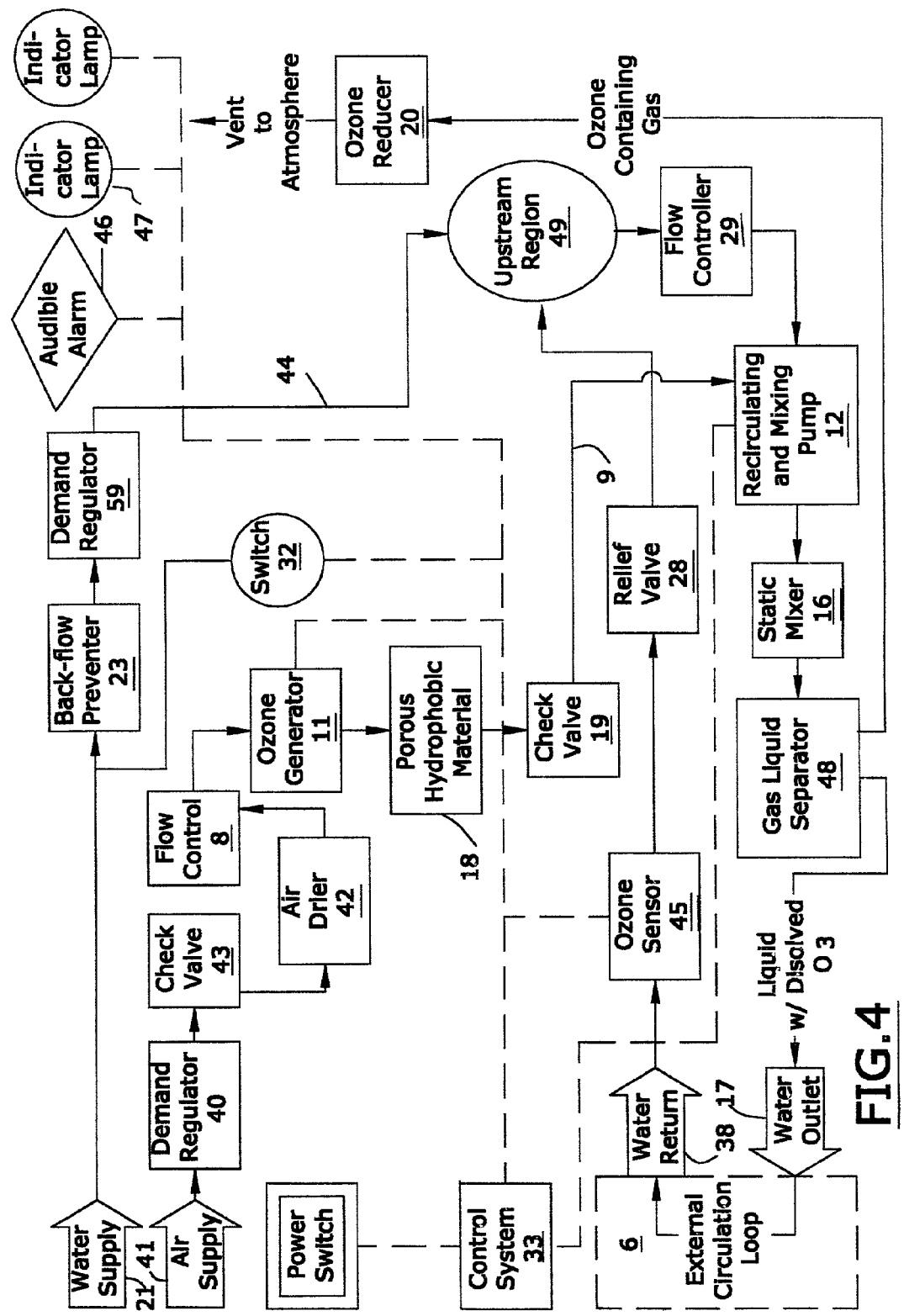

| | | | |
|---|---|---|---|
| 5,942,125 A * | 8/1999 | Engelhard et al. | 210/748 |
| 5,945,068 A | 8/1999 | Ferone | 422/28 |
| 6,019,905 A | 2/2000 | Waggoner | 210/739 |
| 6,607,695 B2 * | 8/2003 | Vellutato | 422/22 |

FOREIGN PATENT DOCUMENTS

| | | |
|---|---|---|
| JP | 2000308815 | 7/2000 |
| JP | 2001044162 | 2/2001 |
| WO | WO0064568 | 11/2000 |

OTHER PUBLICATIONS

International Report on Patentability of PCT/US02/04735 which corresponds to U.S. Appl. No. 10/074,992.

A machine translation of JP2001-044162.

A machine translation of JP2000-308815.

Prosecution history between Jan. 19, 2010 and Jan. 24, 2011 for Canadian patent application CA2437486 which corresponds to subject U.S. Appl. No. 10/074,992.

* cited by examiner

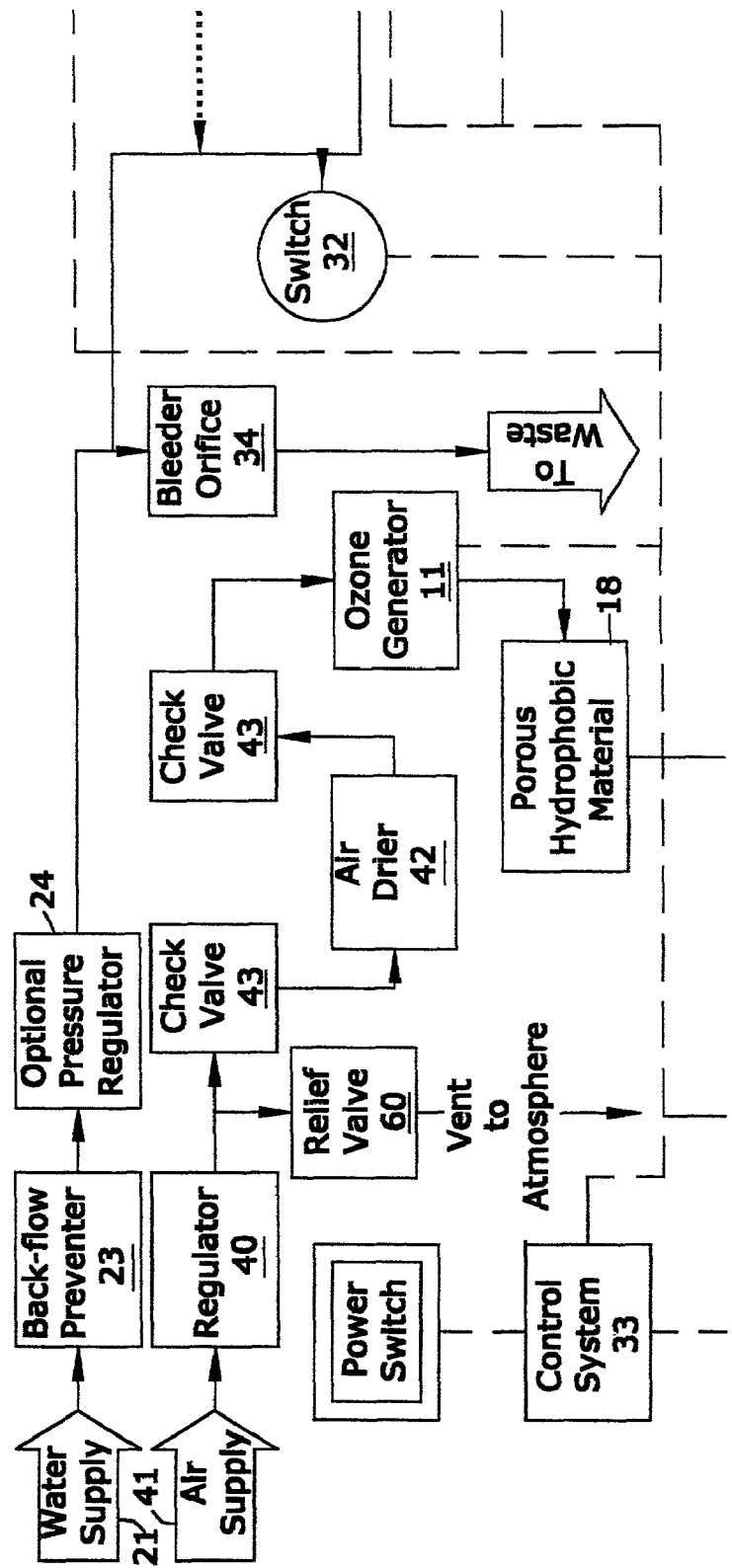
FIG.1-a

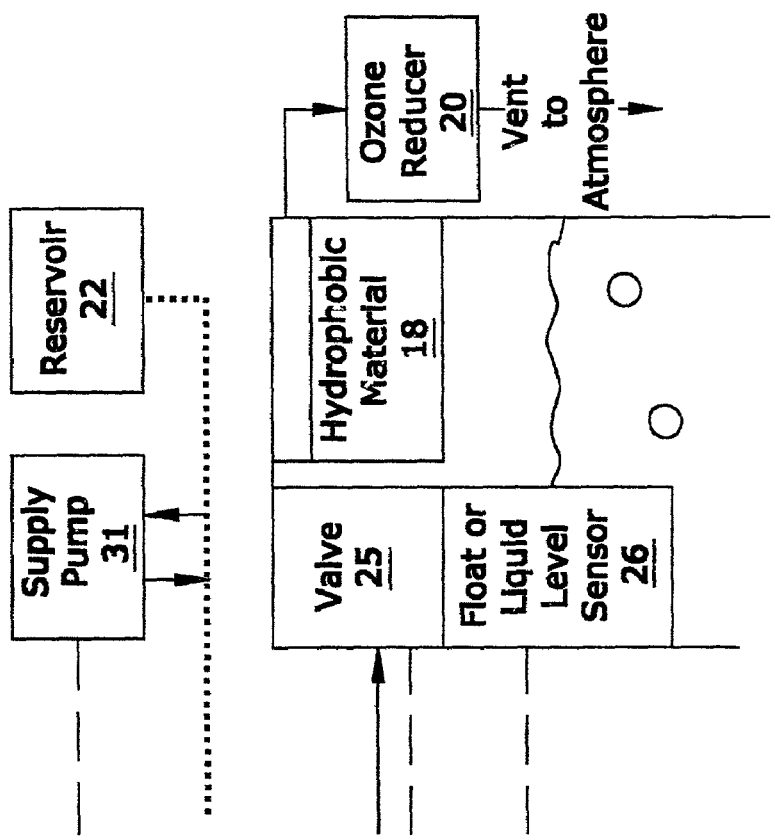
FIG.1-b

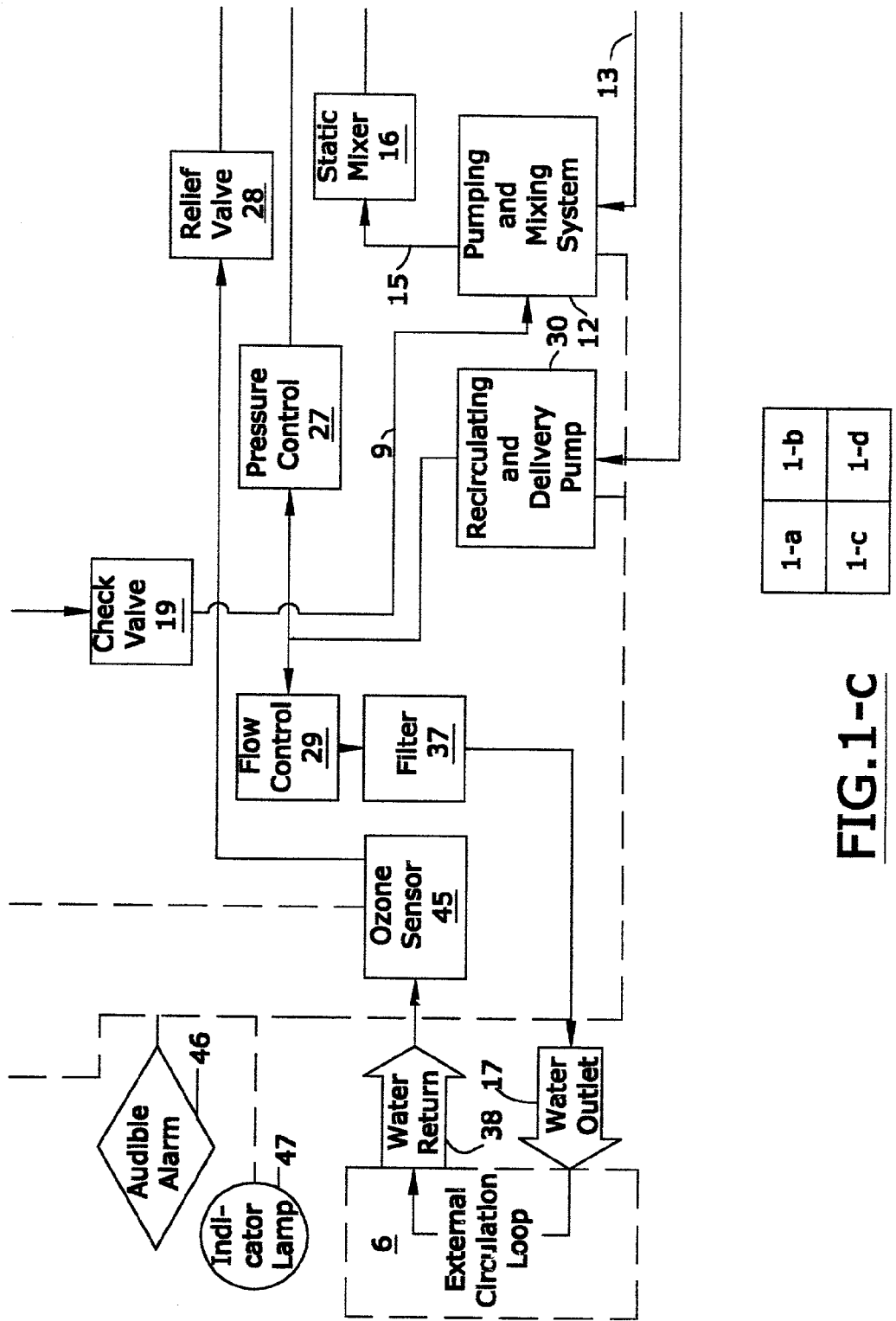
FIG.1-c

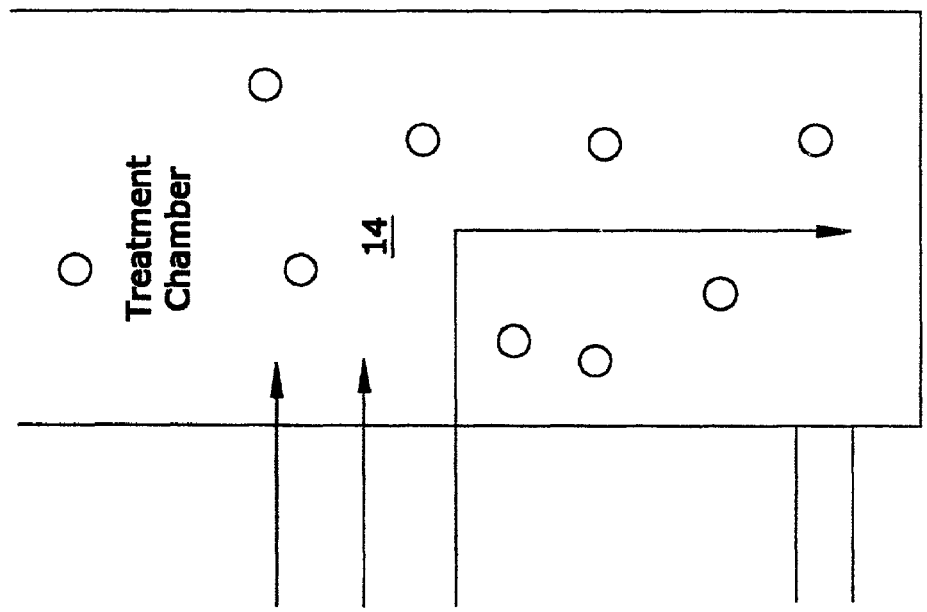
FIG.1-d

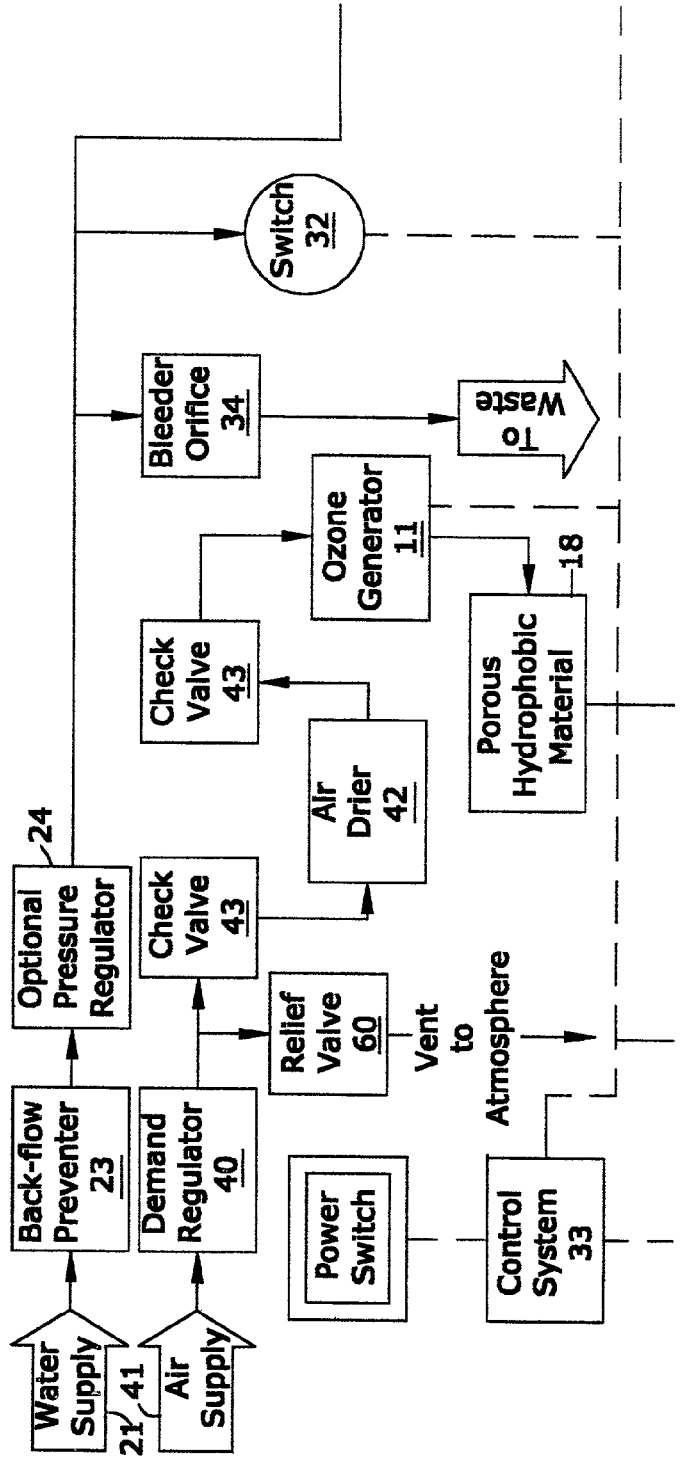
FIG.2-a

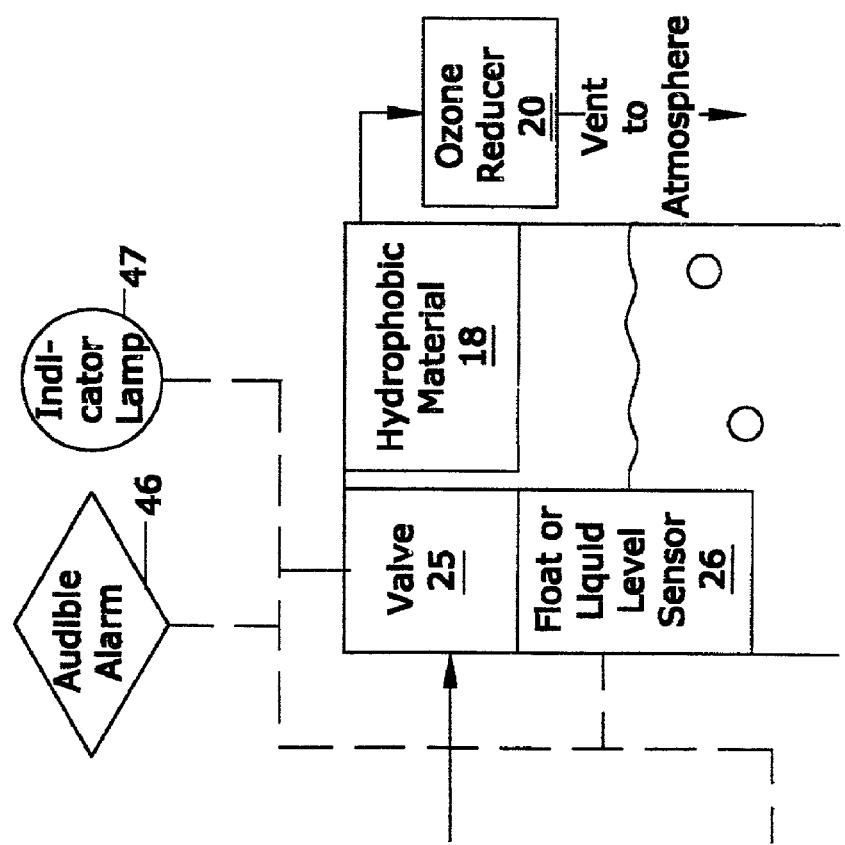
FIG.2-b

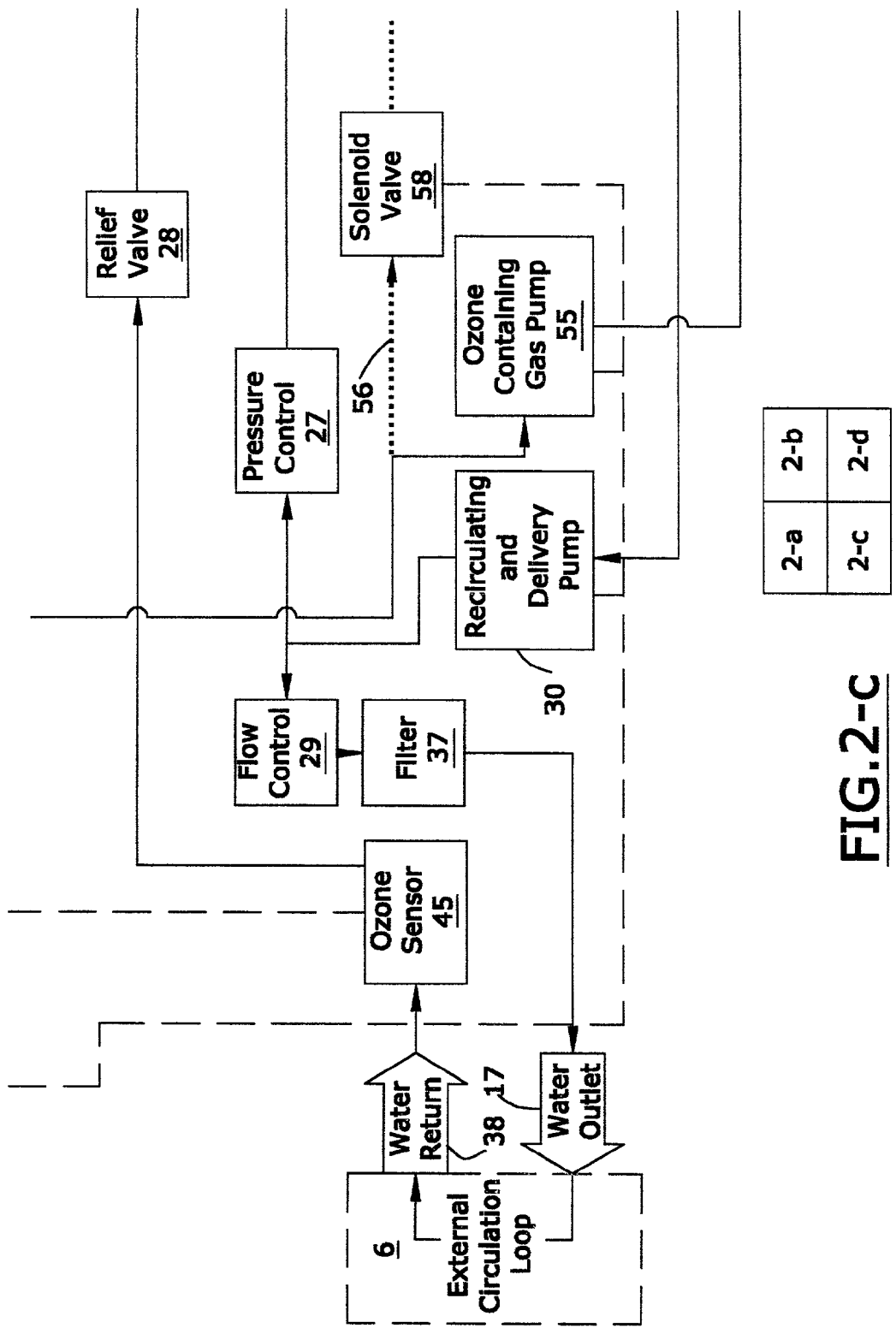
FIG.2-C

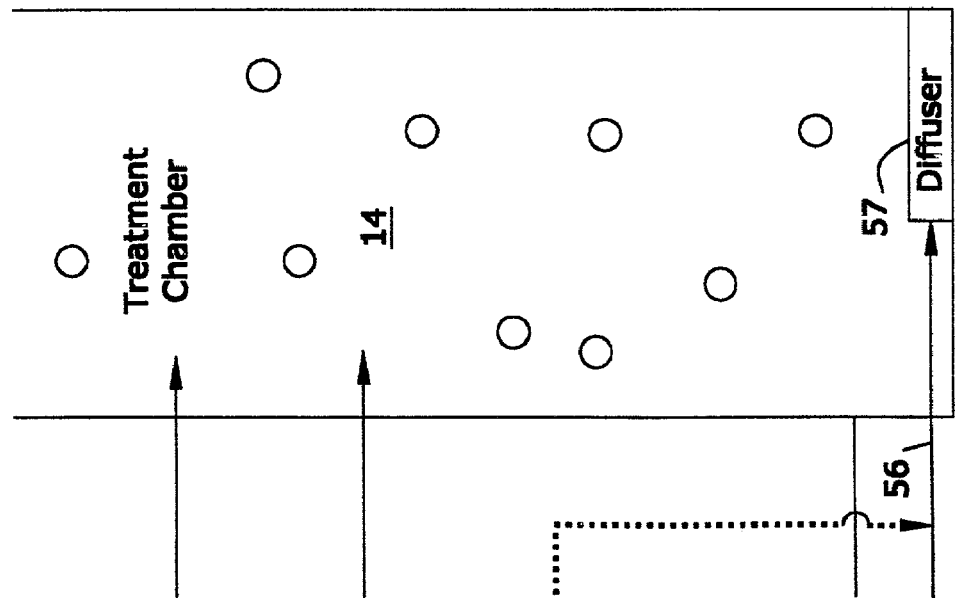
FIG.2-d

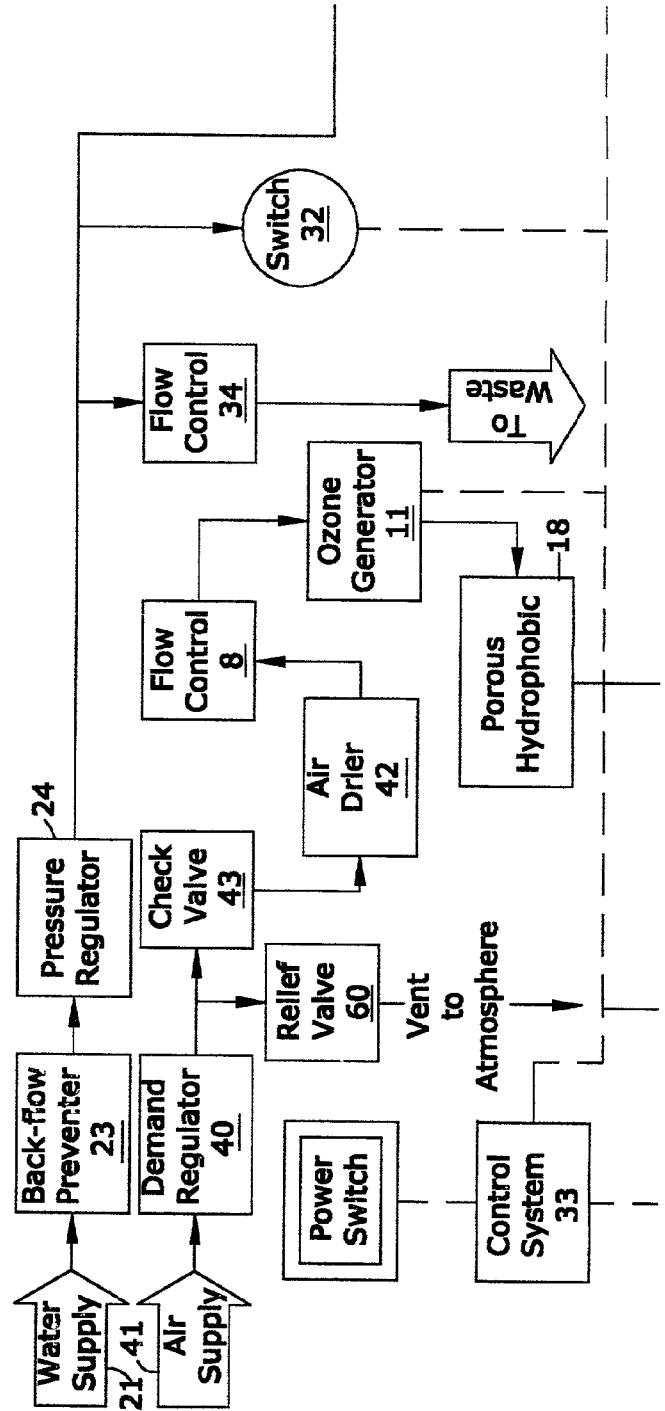
FIG.3-a

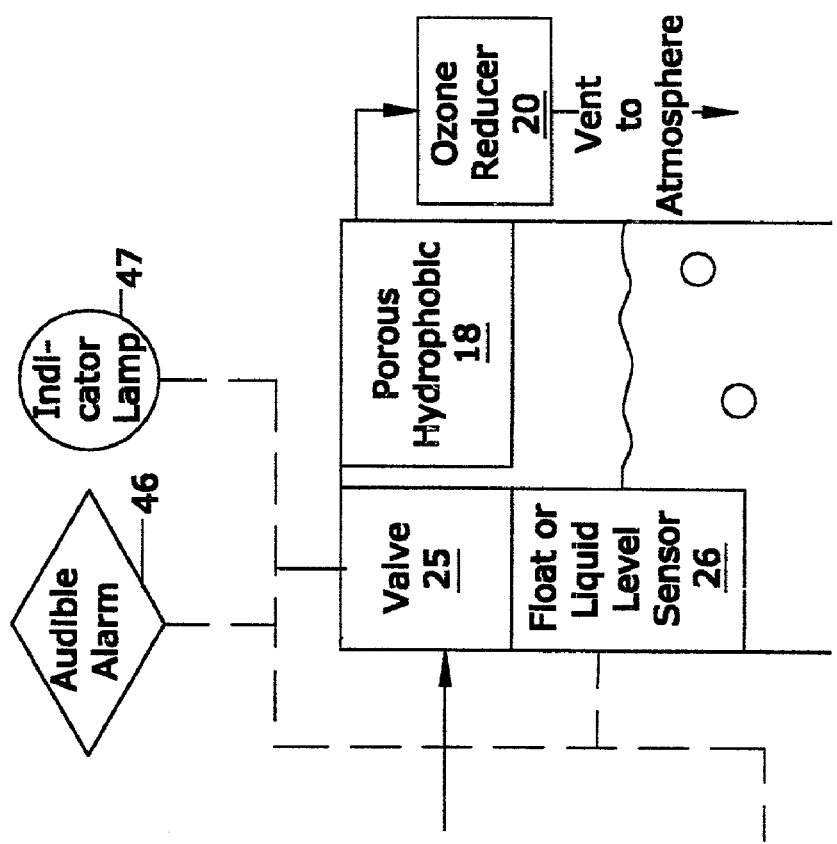
FIG.3-b

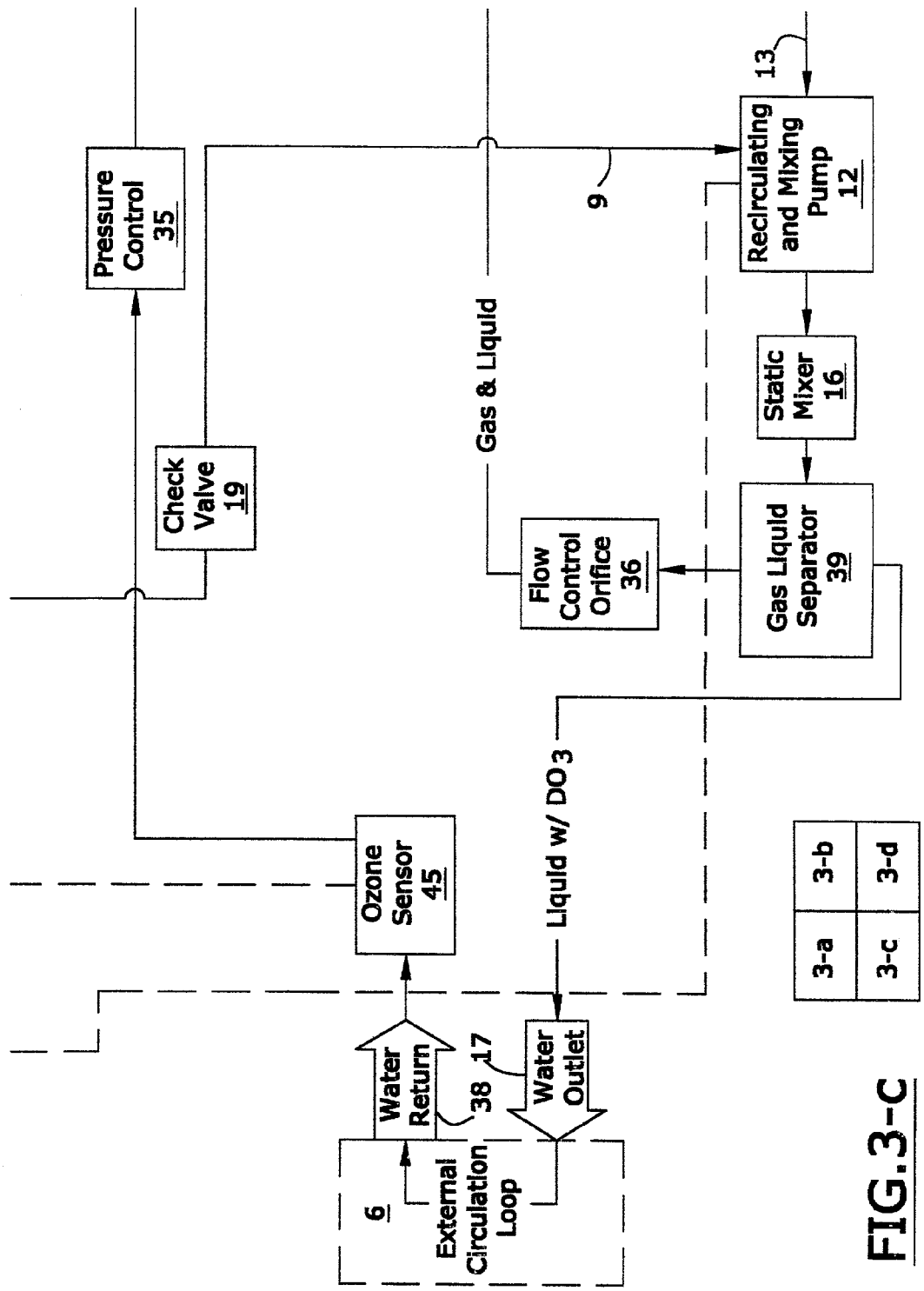
FIG.3-C

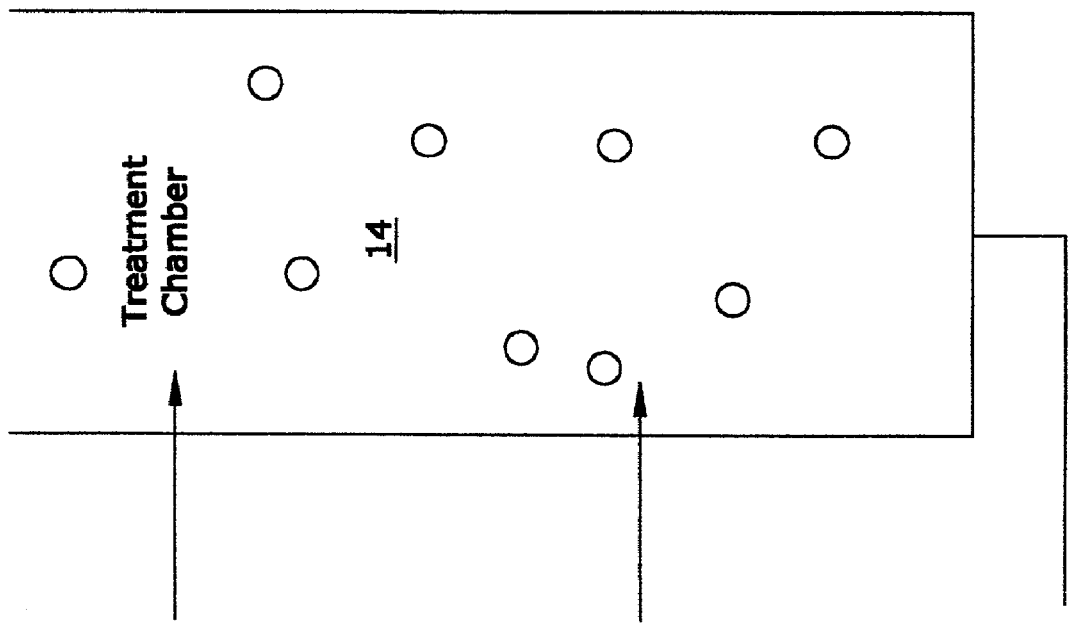
FIG.3-d

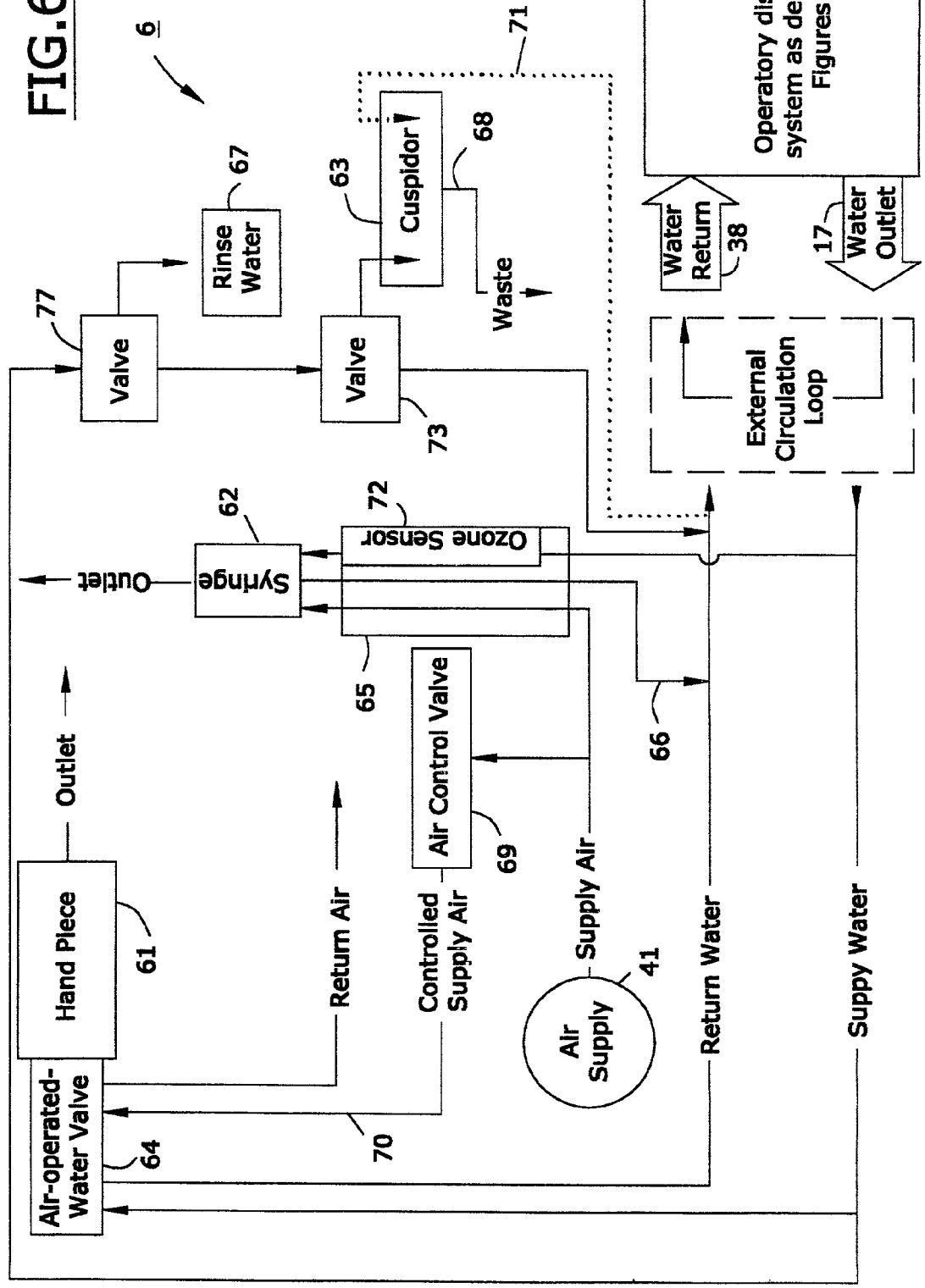

OPERATORY WATER DISINFECTION SYSTEM

This application claims the benefit of U.S. Provisional Application No. 60/269,403, filed on Feb. 16, 2001, which provisional application is incorporated by reference herein.

TECHNICAL FIELD

Ozone disinfection of operatory water lines, in particular dental operatory unit water lines.

BACKGROUND

There has been serious concern that microbial contamination of dental office water systems puts dental patients at risk of diseases. The problem of water contamination, especially when due to cross contamination from other patients, is greatest for patients with weak immune systems. Additionally, dental water can become contaminated from the water supply. More commonly, contamination results from growth of microbial biofilms on the inner surface of water lines. Such biofilms can include germs introduced from patients. Germs can slough off from biofilms as water passes through water lines. Thus, it is not uncommon for water coming out of dental hand pieces to have more than one million bacteria per milliliter while the water entering the dental lines has less than 100 bacteria per milliliter.

Existing systems do not remove microbial biofilms, do not provide failure warning are inconvenient, are expensive, require excessive dental labor and depend on perfect user compliance with manufacturers' instructions.

SUMMARY OF THE INVENTION

Our invention makes possible a small, low-cost and user-friendly ozone appliance for the professional dental office and other medical applications. It is based in part on the advantages gained in using dissolved ozone as a disinfectant. Ozone dissolved in water can not only disinfect water and water lines, it can also reduce gum bleeding, gingivitis, bad breath, teeth stains and oral bacteria. Additionally, it can aid in wound disinfection in surgery. Our invention introduces dissolved ozone into dental and surgical operatory water lines. This dissolved ozone attacks microbial contamination of water from dental and surgical operatory water lines and attached hand pieces and dispensing devices. Our system automatically kills waterborne germs and destroys biofilms where germs can hide and grow. It can, therefore, be used to disinfect water lines in dental operations and for other medical applications such as providing liquid containing ozone for cleaning and disinfecting skin prior to surgery (and tissue exposed during surgery). We believe it will also be readily applicable in the context of ophthalmic surgery. Further, a unit connected to operatory water lines can give an audible or other alarm if the water becomes unsafe.

Thus, the advantages of our ozone system are numerous. Ozone disinfection via our system is automatic, making it much more convenient for dental personnel. With our system, ozone disinfection automatically adjusts for variable water flow and quality. Further, ozone containing gas is separated from the water before the water is circulated with excess ozone converted to oxygen before venting. Moreover, ozone disinfection using our system does not depend on strict user compliance as our ozone system provides failure warning. In addition, ozone is the only disinfectant that can inactivate all pathogens in a short time. Ozone can destroy endotoxins produced by bacteria and destroy biofilms. (Microorganisms do not develop resistance to ozone). Finally, ozone is user friendly. It does not cause allergic reactions, has no offensive taste, and will not cause problems if accidentally ingested (unlike other disinfectants). It also stops gum bleeding and disinfects wound sites.

DRAWINGS

FIGS. 1-5 are schematic diagrams of different embodiments of the inventive operatory water disinfection systems having many components in common.

FIG. 1 schematically illustrates a first embodiment of our invention.

FIG. 2 schematically illustrates a second embodiment of our invention. The system of FIG. 2 differs from the system of FIG. 1 primarily in the way the ozone-containing gas is contacted and mixed with the water.

FIG. 3 schematically illustrates a third embodiment of our invention. The system of FIG. 3 differs from the system of FIG. 1 primarily by economizing the mixing and delivery processes with fewer components.

FIG. 4 schematically illustrates a fourth embodiment of our invention. The system of FIG. 4 differs from the system of FIG. 1 primarily by economizing the mixing and delivery processes with fewer components.

Figure 5:
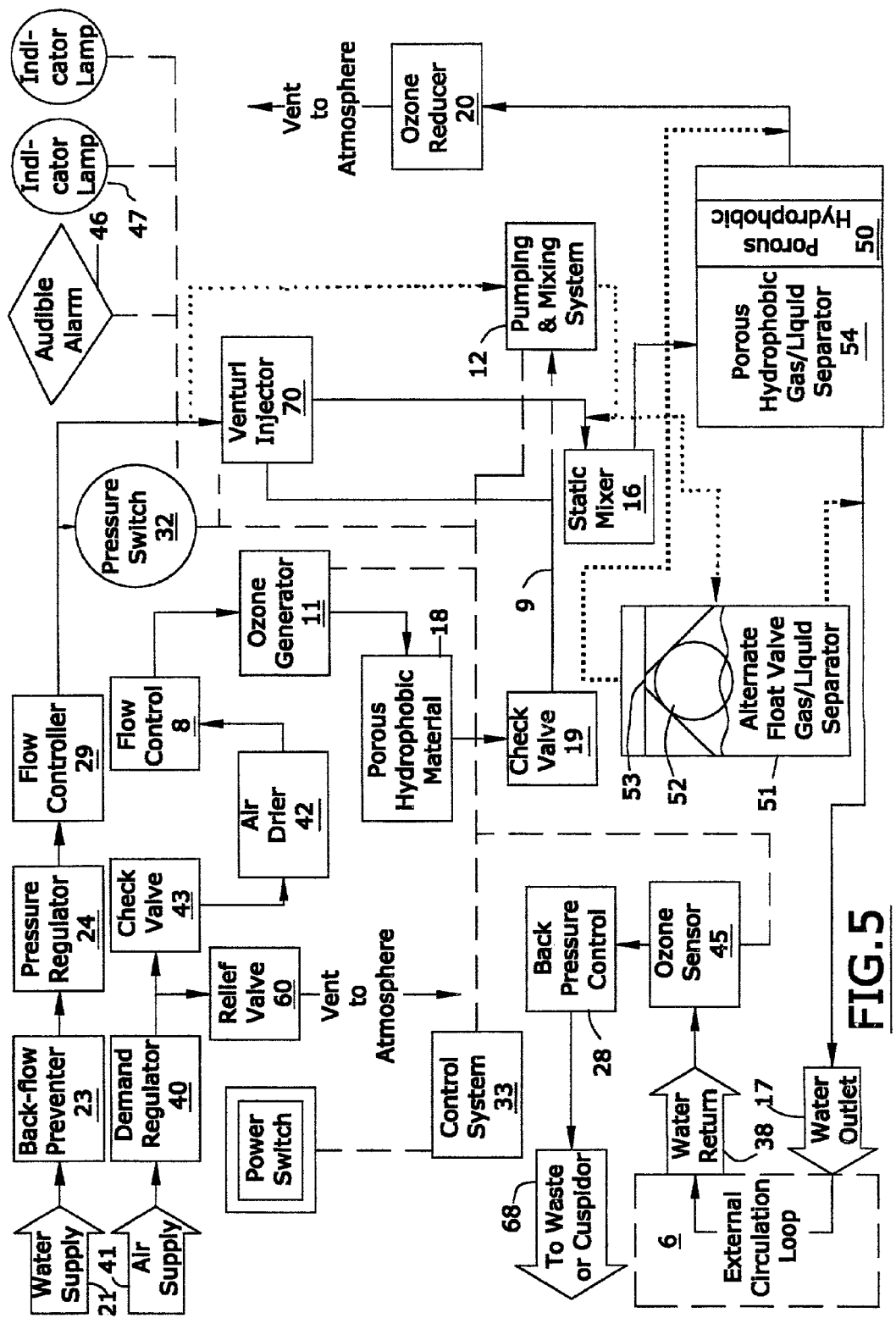

FIG. 5 schematically illustrates a fifth embodiment of our invention. The system of FIG. 5 differs from the system of FIG. 1 primarily by economizing the mixing and delivery processes with fewer components.

FIG. 6 provides a schematic diagram of a preferred external circulation passageway enhancing the operation and effectiveness of the inventive operatory disinfection system.

DETAILED DESCRIPTION

The preferred embodiments of the drawings have comparable advantages in features such as convenience, reliability, safety, cost and size. Different embodiments, using different combinations of such features, may be preferred for different users with different requirements. In addition, some of the different features that are illustrated in the drawings can be interchanged among the various embodiments, and the drawings are arranged to illustrate the different features that can be combined and not to delimit one combination of features from another.

Our description will assume that the apparatus is installed in a dental operatory. The invention will first be explained relative to the embodiment illustrated in FIG. 1 and the detail illustrated in FIG. 6. The order of presentation will follow the flow passageways of the ozone-containing gas, the liquid and ozone-containing gas mixing system and the ozonated liquid delivery system. This will reveal aspects of the invention in an order that is understandable but differs from the order of importance of the features involved.

First, the device generates an ozone containing gas using corona discharge, preferably using the corona discharge generator 11 disclosed in Burris' U.S. Pat. No. 5,529,760. The corona discharge method is preferred over the ultraviolet (UV) method, because it can produce the much higher gas ozone concentration needed to achieve an ozone concentration in the liquid adequate for disinfection. The device dissolves the ozone in the liquid by mixing continuously during operation. (See mixing methods disclosed in Burris' U.S. Pat. Nos. 4,555,335; 5,207,993 and 5,213,773.) Our preferred mixing method uses a positive pressure pump 12 (such as a piston, rotary vane, diaphragm, or, preferably, a gear pump) in a liquid bypass. In the bypass mixing method, a liquid line 13 from the treatment chamber 14 and the line 9 from the ozone generator 11 come together at the pump 12 inlet. The mixing pump 12 mixes the ozone-containing gas and liquid and pumps both through the bypass line 15, which preferably includes a static mixer 16 back to the treatment chamber 14.

The air used to generate ozone is preferably first dried to a low dewpoint to improve the efficiency of ozone generation. This may be accomplished by use of replaceable desiccant cartridges 42 or an air drying system. Replaceable desiccant cartridges 42 can be protected from loss of drying capacity by entry of moist air when the system is not operating through the use of spring-loaded check valves 43 at the entrance and exit passageways to the cartridge. It would be advantageous to make use of the operatory supply of dry air 41 through regulator 40 to provide reduced dew point air for use in generating ozone in the device. This would also extend the life of the desiccant. More expensive sources for generator supply gas are oxygen generators or replaceable oxygen tanks. The use of oxygen instead of air greatly increases the ozone generator 11 efficiency and ozone output.

With a constant flow of ozone containing gas in excess of what can be dissolved according to Henry's law, the ozone concentration in the liquid is maintained at the desired level during the operation of the device. One of the great advantages of ozone is that according to Henry's law, the dissolved ozone concentration is determined by the partial pressure of ozone in the gas rather than the amount of ozone so long as there is an excess of ozone.

The ozone containing gas is separated from the liquid after mixing, preferably by gravity in the treatment chamber 14. The alternative methods of using a porous hydrophobic material 54 or a float valve 51 will be discussed in more detail relative to FIG. 5. The separated gas is passed through an ozone reducing material 20 before the gas is released to the atmosphere. Thus, no ozone gas is released from the device to the atmosphere, and bubbles are eliminated from the liquid output line where they might cause problems. The gas/liquid separation is preferably conducted at minimal pressure to reduce the solubility of the gas and the tendency of bubble formation after the liquid is outputted to atmospheric pressure. Liquid is prevented from entering the ozone generator 11 preferably by use of a porous hydrophobic material 18 or a check valve 19. Liquid is preferably prevented from entering the ozone reducing material 20 by use of a porous hydrophobic material 18 or 50. The use of porous hydrophobic materials, such as polytetrafluoroethylene, eliminates moving parts and thus improves reliability.

The liquid supply can be either a pressurized water line 21 or a reservoir 22, which can be refilled or changed when the liquid supply runs low. The liquid from a pressurized water line 21 should be connected according to locally accepted practices through back flow preventers 23 and pressure regulators 24 as required, all of which are well known in the industry. The liquid from a pressurized water line 21 can be admitted to the operatory disinfecting system by a valve 25, responsive to a float or liquid level sensor 26, as needed to replace outputted liquid. Admission of replacement liquid from a reservoir 22 can be controlled by a valve 25 as with a pressurized water line 21 or in the case where gravity will not be adequate, a pump 31 responsive to a float switch or liquid level sensor 26.

It is common for dental offices to have a master water valve that is shut off when there are no patients being treated in the office. In the event of the contents of the reservoir 22 being consumed or the water system 21 turned off (by a master control valve in the facility) a pressure switch 32 or sensor can communicate with the control system 33 to signal a shortage of liquid supply and or shut down the operatory disinfection system. If the pressure switch 32 is to be relied upon to shut down the operatory disinfecting system, we prefer that a bleeder valve or orifice 34 be installed in the supply line 21 upstream of valve 25. This arrangement eliminates the possibility of the system remaining on after the water supply 21 is turned off. This situation can occur if no liquid is required by the operatory disinfecting system to run down the pressure of the supply line 21. Alternatively, a sensor, such as liquid level sensor 26, can communicate with a controller 33 to determine that the system has not put out any liquid for a predetermined period of time and can shut down the operatory disinfecting system, it is preferred that a warning is given prior to actually shutting the system down.

Second, the liquid containing dissolved ozone is outputted from the dissolving system at a controlled constant rate and pressure to points as close as possible to the outlets to atmospheric pressure. The pressure and flow rate in the circulating liquid line is regulated by appropriately sizing the liquid passageways and the circulating pump 30 (if used) or by use of devices such as pressure regulators 27, pressure relief valves 28 and flow controllers 29. The liquid not demanded by dental hand pieces 61, syringes 62 and rinse cups 67 could be either recirculated to the mixing system at liquid return 38 or discarded as waste as shown in FIG. 6. A preferred and beneficial point of discharge as waste, via alternative line 71, is the cuspidor 63, this provides an air gap to the waste line 68 and allows ozonated liquid to flush and rinse the cuspidor 63. With the flow of liquid containing dissolved ozone the objective is to prevent significant delays between ozonating and final use to avoid ozone concentration reduction caused by ozone reversion to oxygen. Ozone dissolved in water has a half-life of approximately 15 minutes before the ozone reverts to normal oxygen. Recirculating and reozonating the liquid has the advantage of requiring a smaller ozone generating and mixing system and providing more holding time to increase germ killing in the liquid. Discharging the ozonated liquid to waste has the advantage of possibly eliminating the circulation pump 30. In either design, the concept is that when the device is turned on to make available ozonated liquid, the system operates continuously to produce more freshly ozonated liquid than the maximum that might be required. If desired, due to water quality considerations, a filter 37 can be added to the water inlet line and/or to the pressurized liquid circulating passageway.

The dental office disinfection system preferably should be installed in each operatory at the point where water is connected to the chair or treatment apparatus. Preferably, as detailed in FIG. 6, the flexible tubing 65 connecting the treated water supply to the hand pieces 61 and syringes 62 should have an extra lumen 66 so that ozonated water can be circulated continuously through the tubing. This would bring freshly ozonated water as close as possible to the point of use. In situations were the control valves are remotely located from the hand pieces 61, it would be beneficial to have the liquid valve 64 located at the hand piece 61. One way to accomplish this is to make use of the commonly used foot operated control valve 69, which controls the air supplied to the turbine of the hand piece 61. In this arrangement, a relay valve 64 is actuated according to the air pressure received to determine the flow of liquid to the hand piece 61. For example, as more air pressure is applied (faster turbine speed, more heat is generated) more liquid is dispensed (for greater cooling).

Ideally, an ozone sensor 45 would be in the treated liquid passageway. The ozone sensor circuit would provide assurance that the system is operating properly or warn if it is not. For example, the sensor circuit could activate an alarm such as a beeper 46 and or a lamp 47 if the ozone concentration falls too low. In practice, this alarm could activate briefly each morning after the system was turned on, and then activate only if there were a problem with the system. Another possibility is that after a time delay to get the system started, the sensor in communication with the controller 33 could prevent liquid outputting if the ozone concentration fell below an established minimum level. An alternate or additional ozone sensor 72 would be as close as possible to the point of use (possibly made as part of the hand piece 61 or syringe 62) and further it could be powered by battery or the sensor current to indicate to the user that ozone is present in the liquid or not. One possible way for the sensor 72 to communicate with the user is through a two-color light emitting diode where red indicates insufficient dissolved ozone and green indicates sufficient dissolved ozone. The ozone sensor could use an ORP (Oxidation Reduction Potential) electrode, which is well known to those skilled in the art, or preferably, two dissimilar (with different positions in the electromotive series) metals in the liquid stream connected to generate a galvanic potential proportional to the ozone concentration. While use of an ozone sensor 45 to warn of system problems should be adequate, additional sensor circuits to warn of low liquid pressure or flow rate could be added for additional safety.

The embodiment of FIG. 2 is substantially similar to the embodiment of FIG. 1, but differs in the way ozone-containing gas is introduced and mixed with the liquid. Specifically the mixing pump 12 along with static mixer 16, bypass passageway 15 and inlet passageway 13 has been replaced with an ozone-containing gas pump 55, an ozone-containing gas passageway 56 and a gas diffuser 57. The diffuser 57 is preferably the fine bubble diffuser disclosed in Burris' U.S. Pat. Nos. 5,422,043 and 5,858,283. One advantage of this embodiment is possibly quieter operation. To further quiet and economize the operation, the ozone-containing gas pump 55 can be replaced with a solenoid valve 58 that makes use of the pressure supplied by the operatory air system 41. The air treatment and ozone generator would then be configured for a pressurized application including a pressure relief valve 60 to prevent over pressurizing the gas system. The gas liquid separation, the control system and liquid delivery system remains the same as described with regard to FIG. 1.

The embodiment of FIG. 3 is similar to the embodiment of FIG. 1, but differs in that the functions of the delivery and dissolving systems have been combined to be achieved with one pump. In this arrangement, the mixing pump 12 is configured to mix the ozone-containing gas and liquid, the gas and liquid mixture then preferably enters a static mixer 16 as in the preferred embodiment of FIG. 1. At this point, the gas and liquid mixture are directed to an inline gravity liquid separator 39. All of the gas and some of the liquid exit the upper region of the separator 39 and are directed to the treatment chamber 14. Liquid exits the lower region of the liquid separator 39 and is directed to the exterior circulation passageway 6 as described in reference to FIG. 6. The pump 12 and the passageways are sized to provide the proper flow and backpressure to cause the treated liquid to flow through circulation passageway 6. Alternatively, pressure controls 35 and liquid flow control 36 and gas flow control 8 can be used to direct the gas and liquid on the proper course at the proper pressure and at the proper flow rate.

The embodiment of FIG. 4 further economizes the embodiment of FIG. 3. In this configuration the treatment chamber 14 is eliminated and the apparatus for contacting the ozone-containing gas with the liquid is similar the difference is in the separation of the gas from the liquid. The gas/liquid separator 48, using a float valve or preferably a porous hydrophobic material, separates the gas from the liquid and directs the gas to a passageway leading to an ozone reducing material 20 prior to releasing the gas to the atmosphere. The float valve type of gas/liquid separator 51, as shown in FIG. 5, makes use of a float 52 riding on the liquid in a chamber allowing gas to pass through a valve port 53, when the liquid level drops and blocks the exit of liquid through the valve port 53 when the liquid level rises. A porous hydrophobic gas/liquid separator 54, as shown in FIG. 5, contains no moving parts; instead, it makes use of a porous hydrophobic material 50 resisting the flow of liquid through its porosity due to the low surface energy of the hydrophobic material 50. The liquid only, exiting the gas/liquid separator 48 is directed to an external circulation passageway 6 and is preferably returned to the operatory water disinfecting device through water return 38. Once the circulated liquid is returned to the device, it preferably travels through an ozone sensor 45 and then on to a pressure relief valve 28, which can maintain the backpressure as required for dispensing the ozonated liquid along its circulation passageway 6. At this point, the liquid is joined with the incoming liquid 44 in a region 49 upstream of where the ozone-containing gas and liquid are joined and mixed. This provides for recirculation of the liquid and also results in a higher concentration of dissolved ozone. The supply liquid is provided through a demand regulator 59, this arrangement will also provide a draw from reservoir 22 if so equipped. In this embodiment the flows of the gas and the liquid can be controlled by flow controllers 29, pressure relief valves 28 and orifices 36 but we prefer to use spring loaded check valves 43 and passageways sized according to the requirements for controlling the desired flows.

The embodiment of FIG. 5 further economizes the embodiment of FIG. 4. The two primary differences being: one; the circulated liquid is discharged to waste 68 such as in the cuspidor 63 and two; the mixing pump 12 can be replaced with a venturi injector 70 to add and mix the ozone-containing gas with the liquid. Since the effectiveness of the venturi injector is dependant upon liquid flow, it is preferable to include a pressure sensor 32 to warn of low incoming liquid pressure. It is also possible to make use of the pressure in the oxygen-containing gas supply 41 to aid in mixing the ozone-containing gas with the liquid.

The embodiment of FIG. 6 illustrates in detail the preferred arrangement of the circulation passageway 6 of the inventive device. The treated liquid may also be dispensed to fill the rinse cup 67 and to rinse the cuspidor 63 through valves 77 and 73 respectively. As previously disclosed it is most desirous to place the output valves 62, 64, 73 and 77 and circulate the treated liquid as close to the point of treated liquid discharge as possible. In the non-recirculated version, the liquid can flow through an ozone sensor 45 prior to discharge through alternate passageway 71 as shown in FIG. 5. This way the treated liquid is checked for ozone content at the completion of its intended purpose. The alternate flow passageway 71 can be used when the circulation destination is to waste 68 through the cuspidor 63.

We claim:
1. A device for disinfecting operatory unit water and lines, comprising:
   a liquid source including a pressurized water line or a reservoir;
   an ozone generator using a corona discharge to produce an ozone containing gas;

a protection system that prevents liquid from the liquid source from entering the ozone generator;

an ozone mixing system, said ozone mixing system mixing and dissolving the ozone containing gas in the liquid and producing a quantity of ozonated liquid that is, when the device is operating, greater than the amount that is demanded by the operatory unit;

a continuous circulation system that continuously re-circulates the liquid containing dissolved ozone through a pressurized liquid recirculation passageway connected to and providing liquid containing dissolved ozone to the operatory unit, said circulation system including a back pressure control to maintain pressure sufficient to dispense the ozonated liquid from the recirculation passageway;

a separation system that separates undissolved gas from the ozonated liquid prior to pressurizing and circulating the ozonated liquid through the recirculation passageway;

a reducing system that prevents ozone in the separated gas from escaping into the atmosphere during operation of the device by passing the gas through an ozone reducing material before venting to atmosphere;

a liquid admitting system that inputs liquid from the liquid source into the mixing system to replace liquid output to the operatory unit; and a control system for controlling the device to operate as desired to produce liquid containing dissolved ozone and to recirculate and output liquid containing dissolved ozone, said control system further including an ozone sensor, located in said liquid recirculation passageway, the ozone sensor connected to said control system and said control system further connected to an alarm to indicate whether the device is operating properly.

2. The device of claim 1 wherein said back pressure control is selected from the group consisting of: a pressure regulator, a pressure relief valve, and a flow controller.

3. The device of claim 1 wherein there is at least one connection in the pressurized liquid recirculation passageway for outputting liquid with dissolved ozone.

4. The device of claim 1 wherein said ozone generator is of a capacity sufficient to generate more ozone than can be dissolved in the liquid flow.

5. The device of claim 1 further including a positive pressure pump for further mixing the ozone containing gas with the liquid.

6. The device of claim 1 further including a static mixer for further mixing the ozone containing gas with the liquid.

7. The device of claim 1 further including a gas diffuser for mixing the ozone containing gas with the liquid.

8. The device of claim 1 wherein undissolved ozone containing gas is separated from the liquid by use of a porous hydrophobic material.

9. The device of claim 1 wherein undissolved ozone containing gas is separated from the ozonated liquid at near atmospheric pressure.

10. The device of claim 1 further including a barrier preventing liquid from entering the ozone reducing material.

11. The device of claim 10 wherein said barrier includes a porous hydrophobic barrier.

12. The device of claim 1 wherein the source of the liquid provides pressure to circulate and output the ozonated liquid.

13. The device of claim 1 wherein a pump provides pressure to circulate and output the ozonated liquid.

14. The device of claim 1 further including a waste line, wherein said circulation system circulates the ozonated liquid through the pressurized liquid recirculation passageway and liquid that is not output for use from said pressurized liquid recirculation passageway is directed to the waste line.

15. The device of claim 14 further including a cuspidor draining into the waste line, wherein the ozonated liquid that is directed to a waste line is directed to rinse the cuspidor before entering the waste line.

16. The device of claim 1 wherein a pump for withdrawing liquid containing dissolved ozone from the ozone mixing system recirculates the liquid under pressure through a loop that conducts the liquid back to the ozone mixing system.

17. The device of claim 1 wherein the ozone generator and ozone mixing system are responsive to the ozone sensor.

18. The device of claim 1 wherein a valve controls the rate of output flow of the ozonated liquid.

19. The device of claim 1 wherein a porous hydrophobic barrier is used to prevent liquid from entering the ozone generator.

20. The device of claim 1 wherein the ozone generator uses oxygen to produce an ozone containing gas and where the source of oxygen for the ozone generator is dried air supplied to the operatory unit.

21. The device of claim 1 further including a desiccant, and valves on opposite ends of a cartridge containing said desiccant wherein air is dried by the desiccant, and said desiccant is protected from exposure to moist air by said valves that are closed when the device is not being operated.

22. The device of claim 1 wherein said control system is also responsive to a lack of supply water, for controlling at least the ozone generator and circulation system.

23. The device of claim 1 wherein a filter is installed in the liquid passageway.

24. The device of claim 1 further including a valved dispensing means wherein liquid containing dissolved ozone is recirculated through the valved dispensing means.

25. The device of claim 24 wherein the valved dispensing means is located as near as possible to the point of use and is responsive to air pressure.

26. The device of claim 25 further including a source of the air pressure, said source is connected to drive a turbine in a hand piece.

27. The device of claim 1 wherein the control system, in response to sensing the system has not put out any liquid for a predetermined period of time, shuts the device off.

28. The device of claim 1 further including an ozone sensor in said liquid circulation passageway, located in a return loop of said liquid recirculation passageway after the operatory unit, the ozone sensor connected to said control system and an alarm to indicate whether the device is operating properly.

29. The device of claim 28 wherein the ozone generator and ozone mixing system are responsive to the ozone sensor in the continuous circulation system.

30. A device for disinfecting operatory unit water and lines, comprising:

a liquid source;

an ozone generator using a corona discharge to produce an ozone containing gas;

a protection system that prevents liquid from the liquid source from entering the ozone generator;

an ozone mixing system, said ozone mixing system mixing and dissolving the ozone containing gas in the liquid and producing a quantity of ozonated liquid that is, when the device is operating, greater than the amount that is demanded by the operatory unit;

a re-circulation system, including a pressurized liquid circulation loop connected to the operatory unit, that circulates the liquid containing dissolved ozone through said pressurized liquid circulation loop and to the operatory unit, said circulation loop including a back pressure control to maintain pressure sufficient to dispense the ozonated liquid from the circulation loop at the operatory unit;

a separation system that separates undissolved gas from the ozonated liquid prior to pressurizing and circulating the ozonated liquid through the circulation passageway;

a reducing system that prevents ozone in the separated gas from escaping into the atmosphere by passing the gas through an ozone reducing material before venting;

a liquid admitting system that inputs liquid from the liquid source into the mixing system to replace liquid output to the operatory unit; and a control system, controlling operation of the device and a sensor in communication with the control system, wherein liquid level in a treatment chamber is monitored by the sensor.

* * * * *